United States Patent
Goos et al.

(10) Patent No.: US 9,801,760 B2
(45) Date of Patent: Oct. 31, 2017

(54) TEST DEVICE FOR CALIBRATING A LASER DEVICE

(75) Inventors: Evi Goos, Heroldsbach (DE); Christof Donitzky, Eckental (DE); Christian Wuellner, Moehrendorf (DE)

(73) Assignee: Wavelight GmbH, Erlangen (DE)

( * ) Notice: Subject to any disclaimer, the term of this patent is extended or adjusted under 35 U.S.C. 154(b) by 264 days.

(21) Appl. No.: 14/366,094

(22) PCT Filed: Dec. 13, 2011

(86) PCT No.: PCT/EP2011/006284
§ 371 (c)(1),
(2), (4) Date: Jul. 17, 2015

(87) PCT Pub. No.: WO2013/087080
PCT Pub. Date: Jun. 20, 2013

(65) Prior Publication Data
US 2015/0305937 A1   Oct. 29, 2015

(51) Int. Cl.
| | |
|---|---|
| *A61F 9/008* | (2006.01) |
| *B23K 26/06* | (2014.01) |
| *B23K 26/70* | (2014.01) |
| *A61B 17/00* | (2006.01) |
| *A61B 18/00* | (2006.01) |

(52) U.S. Cl.
CPC ...... *A61F 9/00802* (2013.01); *B23K 26/0626* (2013.01); *B23K 26/705* (2015.10); *A61B 2017/00482* (2013.01); *A61B 2018/00988* (2013.01); *A61F 2009/00855* (2013.01)

(58) Field of Classification Search
CPC ....... G01J 5/522; A61F 9/008–9/00806; A61F 9/00855
See application file for complete search history.

(56) References Cited

U.S. PATENT DOCUMENTS

| | | |
|---|---|---|
| 3,742,182 A | 6/1973 | Saunders |
| 5,520,679 A | 5/1996 | Lin |
| 6,559,934 B1 * | 5/2003 | Yee ..................... A61F 9/00814 356/121 |
| 2002/0026181 A1 | 2/2002 | O'Donnell, Jr. |
| 2002/0120198 A1 * | 8/2002 | Nakamura .............. A61F 9/008 600/473 |

(Continued)

FOREIGN PATENT DOCUMENTS

| | | |
|---|---|---|
| CA | 2735281 A1 | 3/2010 |
| GB | 2355310 | 4/2001 |
| WO | 2004093663 A2 | 11/2004 |

OTHER PUBLICATIONS

Wong et al.; "Surface Characterization of Laser Ablated Hard Tissue: A Comparison of Scanning White Light Interferometry and Electron Microscopy"; proceeding of the Spie, Spie, Jan. 1, 1995; pp. 68-75; vol. 2390.

*Primary Examiner* — Casey Bryant

(57) ABSTRACT

A test device to calibrate the pulse energy of a laser device which provides pulsed laser radiation includes a measuring head with multiple measuring probes. The test device is used in such a way that by means of the laser radiation, multiple test ablations are made on a test surface, in an arrangement corresponding to the relative spatial arrangement of the measuring probes, and the depths of the test ablations are then measured, with simultaneous use of the multiple measuring probes of the measuring head.

7 Claims, 6 Drawing Sheets

(56) References Cited

U.S. PATENT DOCUMENTS

Figure 1:
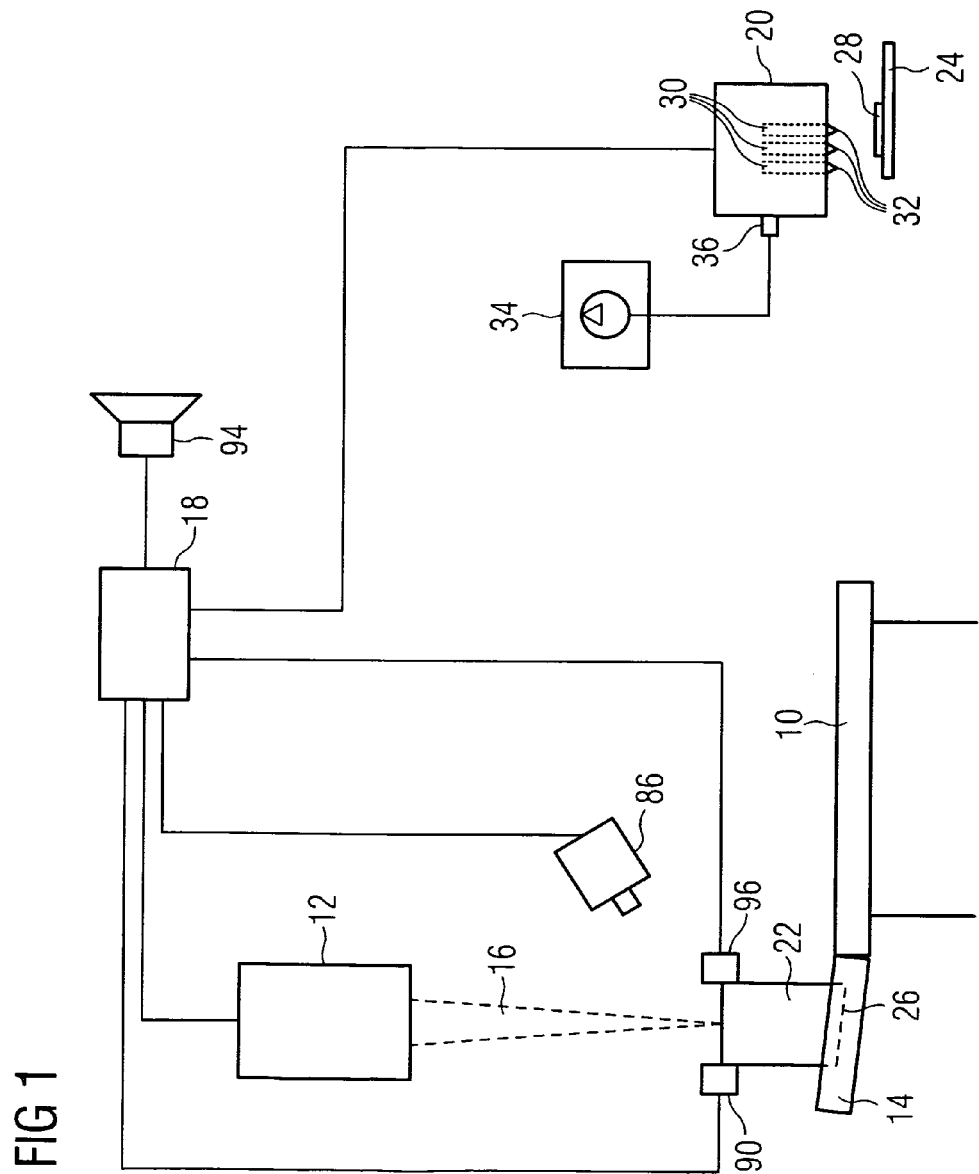

| | | | |
|---|---|---|---|
| 2002/0173711 A1 | 11/2002 | Walton | |
| 2002/0198515 A1* | 12/2002 | Somani | A61F 9/008 356/121 |
| 2003/0016353 A1 | 1/2003 | Detalle et al. | |
| 2003/0040738 A1* | 2/2003 | Ruiz | A61F 9/00808 606/5 |
| 2004/0147910 A1 | 7/2004 | Fujieda | |
| 2004/0260275 A1* | 12/2004 | Liang | A61B 3/1015 606/5 |
| 2005/0024586 A1* | 2/2005 | Teiwes | A61B 3/113 351/209 |
| 2006/0084957 A1* | 4/2006 | Delfyett | A61B 18/20 606/12 |
| 2006/0100613 A1 | 5/2006 | McArdle et al. | |
| 2007/0173797 A1 | 7/2007 | Zickler et al. | |
| 2010/0051793 A1* | 3/2010 | Riedel | G01B 11/22 250/252.1 |
| 2013/0319071 A1* | 12/2013 | Vodnick | G01B 21/047 73/1.08 |

\* cited by examiner

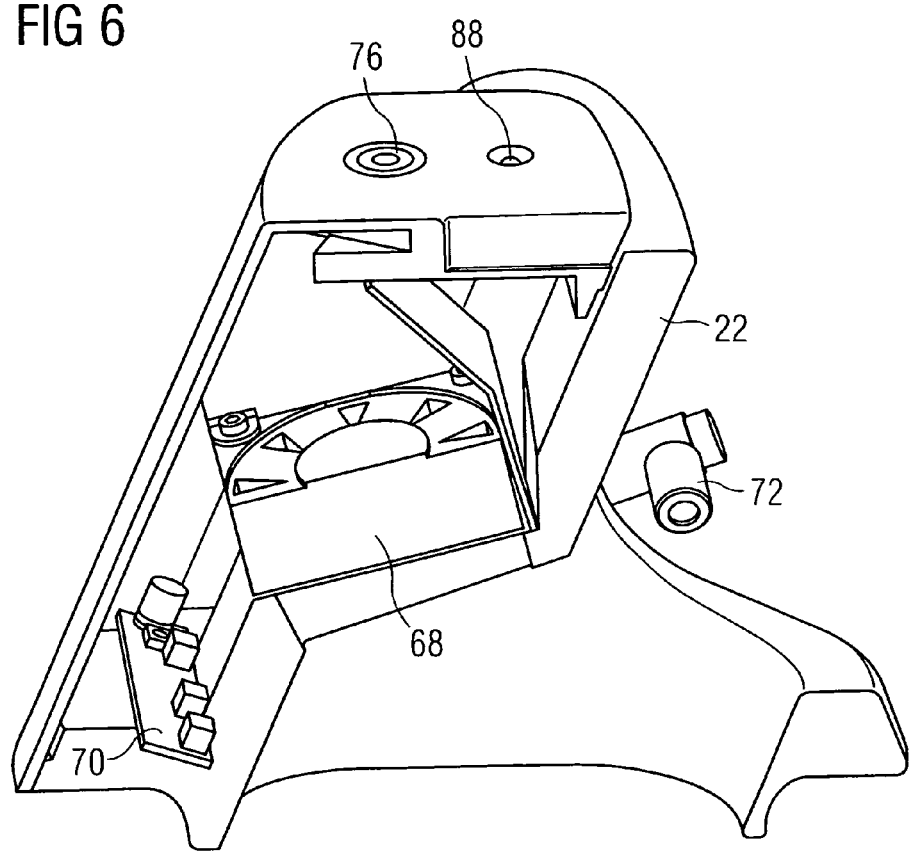

TEST DEVICE FOR CALIBRATING A LASER DEVICE

CROSS REFERENCE TO RELATED APPLICATIONS

This application is a section 371 national stage phase of International Application No. PCT/EP2011/006284, filed 13 Dec. 2011, titled "TEST DEVICE FOR CALIBRATING A LASER DEVICE," which is hereby incorporated by reference in its entirety.

The invention concerns the calibration of a laser device, which for example can be used for laser surgery treatment of the human eye, and there in particular for tissue ablations with laser radiation. In particular, the invention concerns the calibration of the pulse energy of pulsed laser radiation which is provided by such a laser device. For this purpose, the invention provides a test device, which measures the depth of test ablations, which are made on a test surface by means of the laser device in a calibration phase, according to the measuring probe principle.

From WO 2010/022754 A1, a technique for calibrating the energy of laser radiation pulses is already known. In it, on a disc of a test material, multiple test ablations are made by means of the laser radiation, and the depth of the resulting ablation crater is measured without contact, by means of an OLCR measuring device. For each of the test ablations, the pulse energy of the laser radiation is set differently; in this way, a relation can be determined between pulse energy and resulting ablation depth. Then, from this relation, which can be described by a linear equation for example, for a specified setpoint ablation depth an associated setpoint pulse energy can be determined and set on the laser device. In WO 2010/022754 A1, it is also already mentioned that the depth of an ablatively generated test crater can be measured by means of a measuring probe.

An object of the invention is to show a way for a user to calibrate a pulse energy of a laser device, with comparatively little expenditure of time and work.

To achieve this object, the invention provides for using a test device to calibrate the pulse energy of a laser device which provides pulsed laser radiation, the test device including a measuring head with multiple measuring probes. Within the invention, by means of the laser radiation multiple test ablations are made on a test surface, in an arrangement corresponding to the relative spatial arrangement of the measuring probes. The depths of the test ablations are then measured, with simultaneous use of the multiple measuring probes of the measuring head. As proposed in WO 2010/022754 A1, the test ablations are preferably each generated with a different pulse energy of the laser radiation. In particular, each test ablation can be generated by multiple laser radiation pulses, e.g. several hundred or even several thousand pulses. From the measured ablation depths, for example a linear relation between the pulse energy and the ablation depth can then be determined, and the setpoint pulse energy associated with a specified setpoint ablation depth can be determined. Details of this fitting method and the determination of a setpoint pulse energy to be set on the laser device from the relation, determined by fitting, between ablation depth and pulse energy, can be taken from WO 2010/022754 A1, to which reference is expressly made in this respect.

The knowledge of how large the ablation effect in the case of a specified pulse energy is, for example, is necessary for ablative treatment of human cornea tissue by means of UV laser radiation (generated by an excimer laser, for example). Depending on the patient's ametropia to be corrected, a defined, patient-specific ablation profile is calculated, indicating where on the cornea how much corneal tissue is to be removed. Successful treatment is possible only if how much removal results at what energy setting of the laser device is known. The corresponding tests are carried out on a test surface, which usefully consists of a material which in relation to laser radiation behaves similarly to human cornea tissue or at least in a known ratio to human cornea tissue. In particular, the plastic material PMMA (polymethyl methacrylate) has been shown to be suitable for this purpose.

Since in the invention a measuring head which is not just equipped with a single measuring probe, but with multiple measuring probes, is used, simultaneous measurement of the crater depth of multiple test ablations on the test surface is possible. However, assuming a fixed spatial position of the measuring probes relative to each other in the measuring head, care must be taken that the corresponding test ablations on the test surface are generated with the same arrangement as corresponds to the arrangement of the measuring probes in the measuring head. The measuring head, with its multiple measuring probes, makes it possible to measure the test ablations while saving time and work.

In a preferred version, the measuring head includes a total of three measuring probes. However, it is understood that the invention is not restricted to this number of measuring probes, and that instead, in alternative embodiments, two or four or even more measuring probes can be present in the measuring head. The measuring probes considered here usually have a deflectable measuring tip, which can dip into the ablation crater to be measured and is more or less deflected according to the crater depth. The measuring tip can be deflected inductively or capacitively, for example.

According to a preferred embodiment, the test surface is formed by a test disc with a circular outline, the measuring probes being arranged in the measuring head distributed at equal angular intervals along an imaginary circular line. In such a case, in order to ensure that the test disc is guided onto the measuring head at the correct angle of rotation orientation, so that the measuring probes are exactly over the test ablations, both the test disc and the measuring head are preferably implemented with an index marking for angle of rotation alignment relative to each other. The index markings can be implemented as shape or/and colour markings. In particular, the test disc can have, at its disc edge, at least one shape marking, and such a shape marking can be formed from a bevel, a notch or a groove, for example. As a colour marking, any optically perceptible marking which differs in colour from the adjacent areas of the test surface comes into question.

It can be imagined that despite the index markings of the test disc and measuring head, "false" angle of rotation settings in which the test disc can be arranged on the measuring head are possible. In these circumstances, it is then left to the user who does the calibration, while observing the index markings, to guide the test disc onto the measuring head in the correct angle of rotation orientation.

However, it becomes specially simple for the user if the measuring head has a receiving area to receive the test disc, and the index markings of the test disc and of the measuring head allow the test disc to be received in the receiving area only in at least one predetermined angle of rotation position relative to the measuring head. For example, one possibility is that two shape markings which are provided on the test disc and the measuring head can engage with each other only in the predetermined angle of rotation position, and the test disc can therefore be placed in the receiving area of the measuring head only in this predetermined angle of rotation position.

For example, the test disc can have a shape marking which interrupts the circular course of the disc edge, and the receiving area of the measuring head can have a shape marking which is complementary to the shape marking of the test disc. For example, such a shape marking which interrupts the circular course of the disc edge can be in such a form that the edge of the test disc on a part of the disc circumference does not follow the shape of an arc of a circle, but a chord (i.e. conceptually a part of a fully circular disc is broken off).

According to a further development of the invention, the test surface can be formed by a test lamina, the measuring head having a receiving area which is adapted to the shape of the periphery of the test lamina, to receive the test lamina. An evacuation path system, which opens into the receiving area, for connection to a vacuum pump, can then run in the measuring head. The vacuum pump can be housed in the measuring head itself, or the measuring head can have a suitable connecting piece, via which the measuring head can be connected to an external vacuum pump. By applying negative pressure to the evacuation path system, the test lamina can be sucked into the receiving area of the measuring head and held there securely.

The test device can also include an object carrier device, to be set up on or attached to a patient examination table, to hold a test object which forms the test surface (e.g. test lamina, in particular test disc) while the test ablations are applied. In order to be able to apply the test ablations to the test object with a specified arrangement regarding position and orientation relative to the test object, it is advantageous if on the object carrier device and/or the test object an arrangement of multiple (at least two and preferably at least three) marks, which are optically detectable and at a distance from each other, is provided. Within the invention, this mark arrangement can then be captured by means of a camera system, it being possible to determine, from the image data of the camera system, orientation information concerning the mark arrangement, and the shooting positions of the laser device to generate the test ablations being defined depending on the determined orientation information.

The object carrier device can include a basic carrier and an auxiliary carrier, the basic carrier being implemented with first positioning formations for removable positioning of the auxiliary carrier on the basic carrier, and the auxiliary carrier being implemented with second positioning formations for removable positioning of the test object on the auxiliary carrier. Such a two-part version of the object carrier device can be used, in particular, after the test ablations are done, to remove the auxiliary carrier, with the test object lying on it, from the basic carrier, and to bring it to the measuring head. At the measuring head, the test object can then be sucked from the auxiliary carrier by suction force, and sucked onto the measuring head. The user then does not have to take the test object directly in the hand to bring it from the place where the test ablations are generated to the measurement point. This reduces the danger that the test ablations may be contaminated by the test object being touched by hand, or that inevitable ablation dust is unintentionally wiped into the ablation crater by the hand, which would result in falsification of the measurement results.

To place the object carrier device on the patient examination table, it can include a foot part which is adapted to the peripheral contour of a head recess in a head part of the examination table, the object carrier device being inserted with the foot part into the head recess of the examination table to start its operation. In this way, sufficiently stable mounting of the object carrier device is possible. If the object carrier device is equipped with a spirit level, the user can do a certain fine alignment of the object carrier device by observing the spirit level. It is then possible to compensate for remaining positioning imprecision by capturing specified markings of the object carrier device and/or of the test object which is placed on the object carrier device by means of a camera-based eye tracker, and by the shooting positions of the laser radiation for generating the test ablations being automatically adjusted by a control unit of the laser device, depending on the captured position and orientation of these markings.

According to a further development, the test device can include a reading device for reading an identifying code on a test object which forms the test surface, this identifying code being read before the test ablation is done. The identifying code can be in the form of a bar code, for example, and contain a unique identification of the test object or even of the test surface (if one and the same test object provides multiple test surfaces, and correspondingly can be used several times). Each time an energy calibration of the laser device is carried out and test ablations are generated on a test surface, by means of the reading device the relevant identifying code can be read and stored. Then, if a user unintentionally wants to use the same test surface a second time to do test ablations, the reading device, or an external control unit connected to it, can recognise this on the basis of the read identifying code, and for example output an optical and/or acoustic warning signal. An alternative or additional reaction to repeated reading of the same identifying code can be, for example, that the reading device is temporarily blocked against the emission of laser radiation, and only released again when a new identifying code is read, i.e. a test surface which has not yet been used is used.

Alternatively or additionally, the test device can include a marking device for making a marking on a test object which forms the test surface. By means of such a marking, suitable information can be permanently stored on the test object, e.g. information about an instant (e.g. date, time) at which the test ablations were generated on the test object, or/and information about the pulse energy which is used for the test ablations, the number of pulses per test ablation or/and the thus generated crater depths. Such information can be put on the test object in the form of a bar code or in another coded form, for example.

The marking made by the marking device also does not necessarily have to carry information about the test ablations. It is conceivable that the marking device makes only a simple shape or colour marking on the test object before or after generating the test ablations, the thus made marking essentially signalling, as the only information, that the relevant test object or relevant test surface has already been used once, and therefore must not be used again. For example, a notch which was not originally provided on the test object, and is generated by the marking device, can carry this information content. Such a notch or other shape or colour marking can immediately be captured by suitable sensors.

Figure 2:
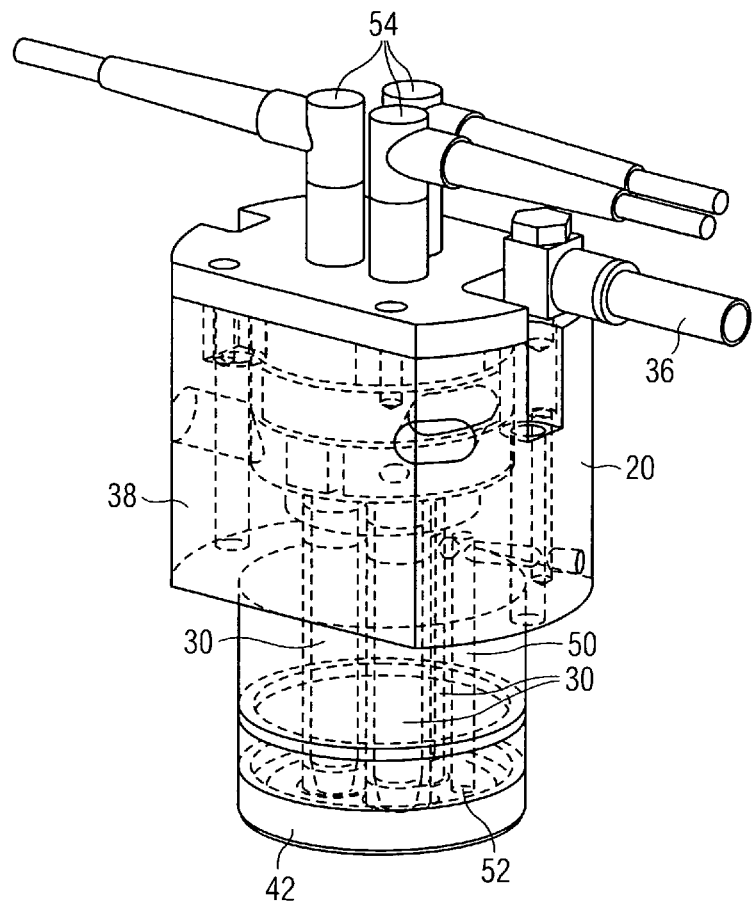
Figure 2:
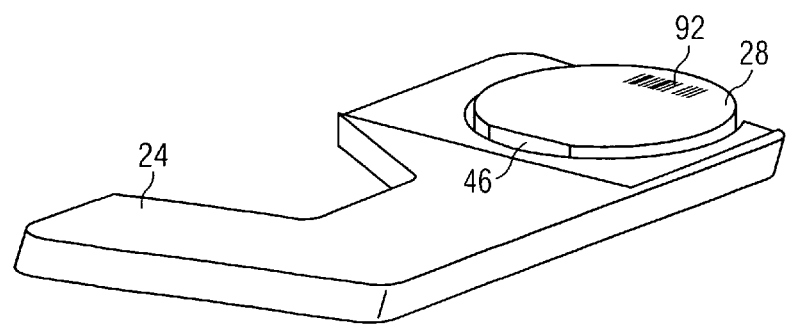
Figure 3:
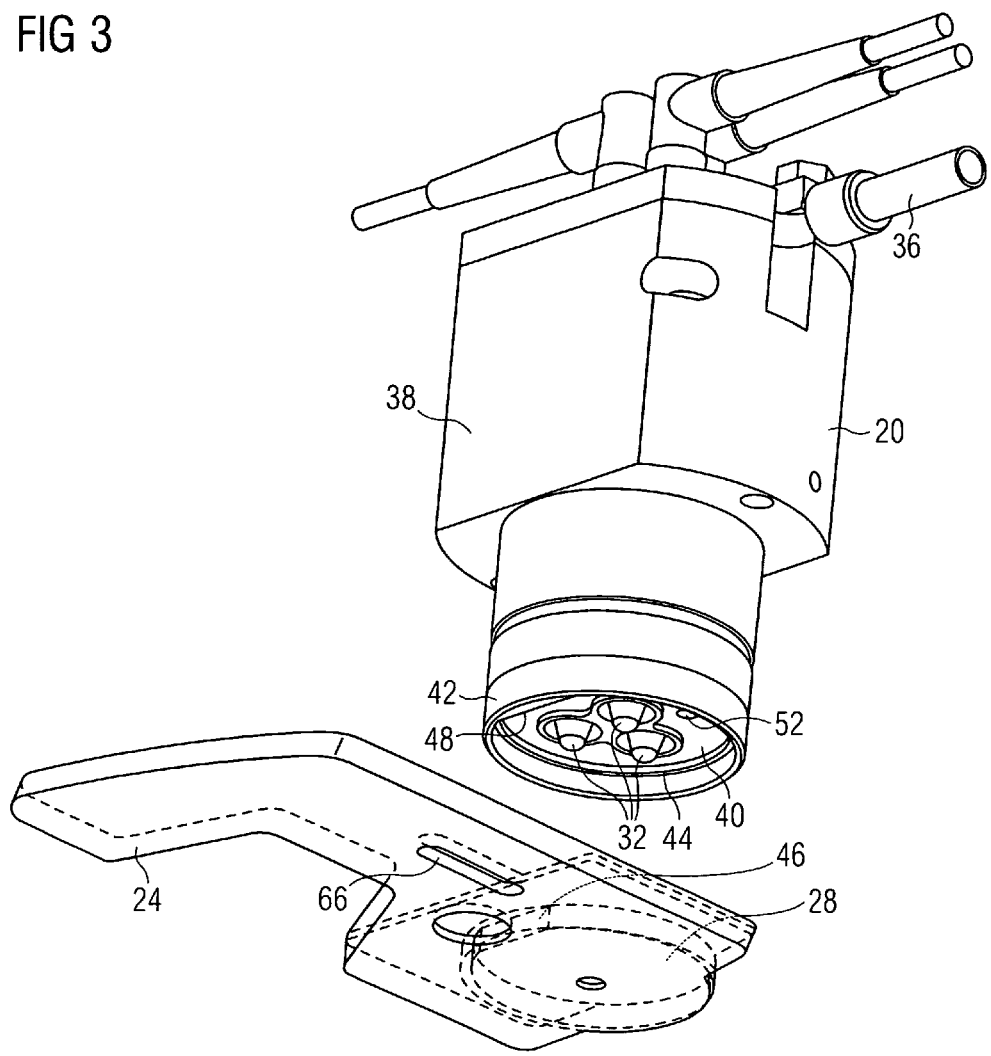
Figure 4:
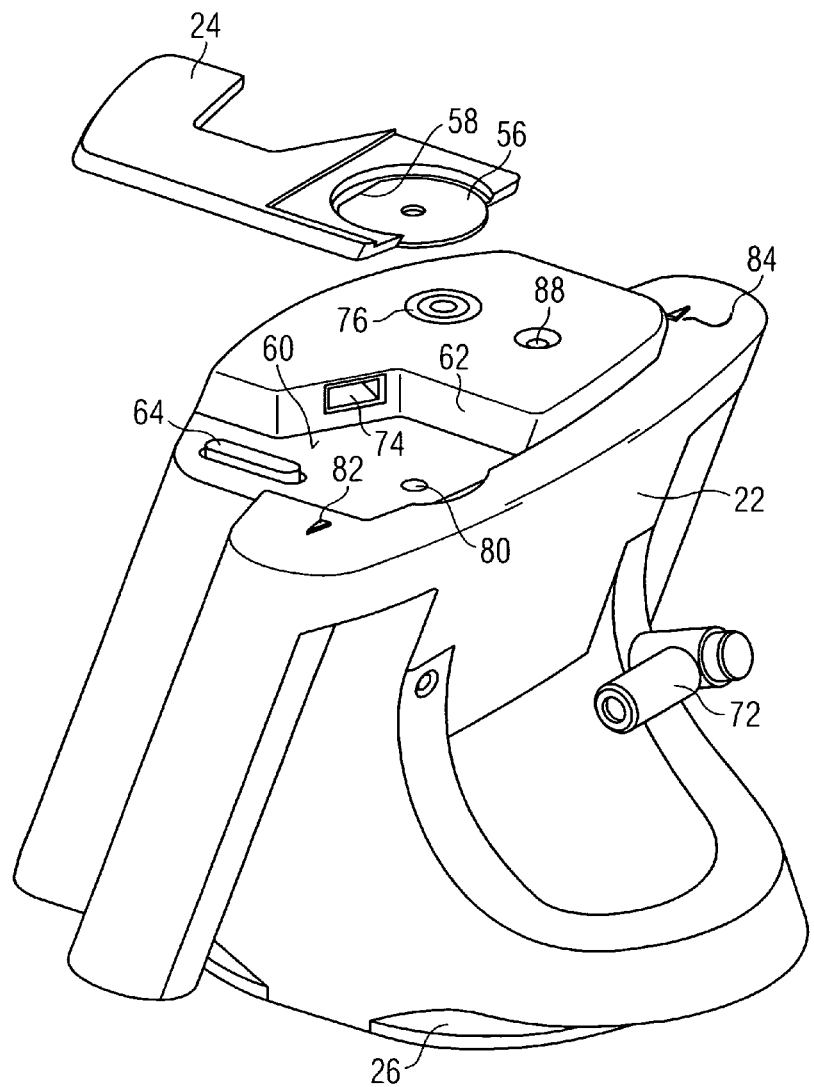
Figure 5:
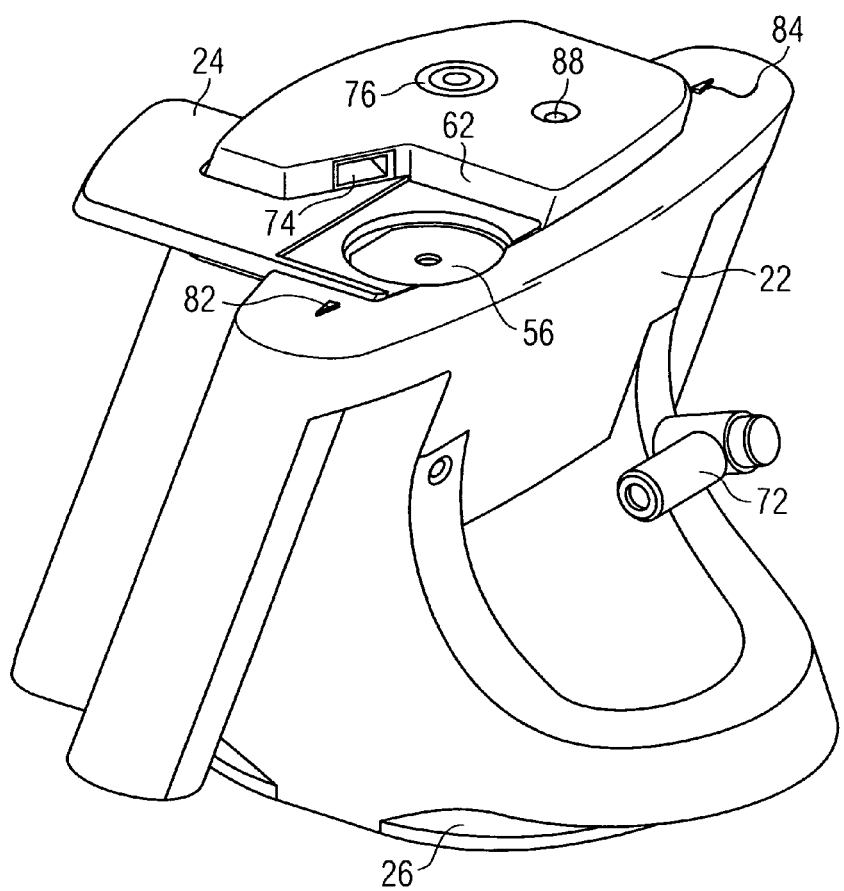

The invention is explained below in more detail on the basis of the attached drawings, of which:

FIG. 1 shows schematically components of a laser device and an associated test device for calibrating the energy of the laser radiation pulses of the laser device according to an embodiment, FIGS. 2 and 3 show various views of a measuring head and an auxiliary carrier for a disc-shaped test object according to an embodiment of the test device, FIG. 4 shows the auxiliary carrier of FIGS. 2 and 3, together with a basic carrier according to an embodiment, the auxiliary carrier and the basic carrier being shown separately from each other, FIG. 5 shows the auxiliary carrier and the basic carrier according to FIG. 4, the auxiliary carrier being placed on the basic carrier, and FIG. 6 shows a cross-section through the basic carrier of FIGS. 4 and 5.

We refer first to FIG. 1. This shows, in a very schematised simplification, an examination table 10, on which a not otherwise shown patient lies, for treating the patient ophthalmologically using a laser device 12. The examination table 10 has a head part 14, which for example is adjustable by swivelling, and on which the patient's head rests. In the representation of FIG. 1, the laser device 12 is shown as the only function block, and includes functional components such as a laser source, focusing optics, scanning components for at least transverse and if required also longitudinal positional control of the laser radiation which the laser device 12 emits, and so on. This laser radiation is preferably pulsed radiation, and for example has a wavelength in the UV range, e.g. about 193 nm. Laser radiation of such a wavelength can be used for ablation of corneal tissue of the human eye, e.g. as part of LASIK treatment (LASIK: laser in-situ keratomileusis). The laser radiation which the laser device 12 emits is shown schematically in FIG. 1 as a focused bundle of rays 16.

The laser device 12 is controlled by an electronic control unit 18, which in the shown example also receives measurement signals from a measuring head 20, analyses these measurement signals, and depending on the measurement results, adjusts the pulse energy of the radiation pulses which the laser device 12 emits.

The measuring head 20 is part of a test device, which additionally includes a two-part object carrier device consisting of a basic carrier 22 and an auxiliary carrier 24. The basic carrier 22 is mounted on the examination table 10. For this purpose, a head recess (indentation or hole), not shown in more detail in FIG. 1, which is typically present in the head part 14 and into which normally the patient puts the back of his or her head, is used. The basic carrier 22 is placed in this head recess, the basic carrier 22 having a foot part 26, the peripheral contour of which is adapted to the contour of the above-mentioned head recess, so that the basic carrier 22 obtains some stability on the examination table 10.

The basic carrier 22 forms a seating, on which the auxiliary carrier 24 can be placed. The auxiliary carrier 24 itself acts as a carrier and holder for a test lamina (test plate) 28, which for example is made of PMMA, and on which, for the purpose of calibrating the pulse energy of the laser device 12, multiple test ablations are done by means of the laser radiation. The test lamina 28 is implemented as a test disc with a circular outline, for example. To do the test ablations, the auxiliary carrier 24, with the test lamina 28 lying on it, is placed on the basic carrier 22, which itself is inserted in the head recess of the head part 14 of the examination table 10. After the test ablations are generated on the test lamina 28, the auxiliary carrier 24 is removed from the basic carrier 22, and together with the test lamina 28 carried to the remotely installed measuring head 20, where for example the auxiliary carrier 24 is guided from below onto a measurement interface of the measuring head 20, until the depth of the test ablations on the test lamina 28 can be measured using measuring probes 30 of the measuring head 20. The measuring probes 30 have deflectable measuring tips 32, which project on the measuring interface of the measuring head 20 and come into contact with the test lamina 28 when this is moved onto the measuring head 20. The test lamina 28 is held firmly on the measuring interface by means of suction force, resulting from a negative pressure which is applied to the measuring interface, said negative pressure being generated by a vacuum source 34, which can be connected to the measuring head 20. For this purpose, the measuring head 20 can have a connecting piece 36, to which the vacuum line leading to the vacuum source 34 can be connected.

Usefully, after the test lamina 28 is measured and the vacuum is switched off, the test lamina 28 is again picked up by the auxiliary carrier 24 and brought to a suitable archiving location, where it is archived. The auxiliary carrier 24 can then be occupied by a new test lamina, and the calibration procedure can begin again. Usefully, such a calibration procedure is always carried out after a relatively long downtime of the laser device 12, during which it is not in operation. For example, the pulse energy of the laser device 12 can be calibrated in a daily rhythm, or even before each laser treatment.

Before further details of the test device are explained in relation to FIG. 1, let preferred embodiments of the measuring head 20, test lamina 28, auxiliary carrier 24 and basic carrier 22 be explained on the basis of FIGS. 2 to 6.

We refer first to FIGS. 2 and 3. According to the example shown there, the measuring head 20 is equipped with a total of three measuring probes 30, which are fitted in a housing 38 and extend with their measuring tips 32 into a receiving area 40, which is adapted to the peripheral contour of the test lamina 28, for the test lamina 28. The measuring probes 30 are in the form of pins, and for example are formed by inductive measuring probes of type designation Millimar P2000 Series of the Mahr GmbH company. The arrangement of the measuring probes 30 is such that their measuring tips 32 are in the corners of an equilateral triangle. This picture can otherwise be expressed as a distribution of the measuring probes 30 at equal angular intervals along an imaginary circular line.

It can easily be seen in FIG. 3 that the receiving area 40, which is open downward, is enclosed by a circular wall 42, the measuring tips 32 not projecting axially (i.e. in the direction of an imaginary ring axis) outward beyond the circular wall 42. On the inner circumference of the circular wall 42, an axially directed annular surrounding limit stop shoulder 44, which delimits the axial insertion depth of the test lamina 28 in the receiving area 40, is formed. The measuring tips 32 extend in the axial direction beyond this limit stop shoulder 44, so that when the test lamina 28 is inserted into the receiving area 40, it pushes against the measuring tips 32, and forces them back until the test lamina 28 comes into contact with the limit stop shoulder 44. According to how deep the ablation craters of the test lamina 28 under the measuring tips 32 are, the measuring tips 32 are deflected to different extents. The deflection is captured in a signal, and passed on to the control unit 18 in the form of an appropriate measurement signal.

The test ablations are generated by means of the laser device 12, under the control of the control unit 18, with the same arrangement on the test lamina 28 as corresponds to the arrangement of the measuring probes 30 relative to each other. That is, a total of three test ablations, which are distributed at equal angular intervals along an imaginary circular line, that is they are in the corners of an isosceles triangle, are generated on the test lamina 28. There is then the problem of ensuring, when the test lamina 28 is inserted into the receiving area 40 of the measuring head 20, that the test lamina 28 has the correct angle of rotation orientation relative to all the measuring probes 30, so that the ablation crater is exactly under the measuring tips 32. For this purpose, the test lamina 28 and the receiving area 40 are implemented with shape markings 46, 48 which are complementary to each other, and which permit insertion of the test lamina 28 into the receiving area 40 in only a single relative angle of rotation orientation. In contrast, in other angle of rotation positions, the test lamina 28 cannot be inserted into the receiving area 40. In the shown example, the form of the shape marking 48 of the test lamina 28 is that a piece (here a segment of a circle) is conceptually cut off the edge of the test lamina 28. Consequently, in the region of this conceptually cut off segment of a circle, the peripheral contour of the test lamina 28 runs along a chord, whereas in the other peripheral regions it runs along a circular line.

In contrast, the shape marking 48 of the receiving area 40 is formed by a circular segment part being provided on the inner circumference of the circular wall 42, corresponding to the circular segment which is conceptually cut off the test lamina 28.

It is understood that other complementary shape markings can be provided on the test lamina 28 and receiving area 40, in order to achieve the desired indexing of a specified, unique angle of rotation orientation of the test lamina 28 relative to the receiving area 40. For example, in the test lamina 28, a hole which is arranged eccentrically to the centre of the lamina, and with which a pin or journal projecting from the floor of the receiving area 40 is associated, could be formed, said pin or journal engaging with the above-mentioned hole in the test lamina 28 when the test lamina is inserted into the receiving area 40 at the correct angle.

Alternatively to complementary shape markings which engage with each other, applying suitable colour markings, which act as optical aids to the user, to the test lamina 28 and measuring head 20 (there on the circular wall 42, for example), in order to find, manually and by eye, the correct angle of rotation orientation of the test lamina 28 relative to the receiving area 40, is conceivable.

The representation (transparent for reasons of draughtsmanship only) of the housing 38 of the measuring head 20 in FIG. 2 allows a view of an evacuation path system which is formed in the measuring head 20, and which runs from the connecting piece 36 to an opening 52 formed on the floor of the receiving area 40. Through the opening 52, when the vacuum source is operated, air is sucked out of the receiving area 40; the suction effect which occurs holds the test lamina 28 firmly in the receiving area 40.

In FIGS. 2 and 3, a total of three electrical connector plugs 54, which for connecting the measuring probes 30 electrically can be connected to the control unit 18 at corresponding plug connections of the measuring head 20, can be seen.

We now also refer to FIGS. 4 and 5. The auxiliary carrier 24 is in the form of a plate part, which has an indented receiving pan 56, into which the test lamina 28 can be inserted. The receiving pan 56 is provided with a shape marking 58 which is complementary to the shape marking 46 of the test lamina 28, and which has the effect that the test lamina 28 can be inserted into the receiving pan 56 only in a single angle of rotation orientation relative to the auxiliary carrier 24. It is understood that as an alternative to shape markings, colour markings can be provided on the auxiliary carrier 24 and test lamina 28, and help the user to align the test lamina 28 in the receiving pan 56 relative to the auxiliary carrier 24 by the naked eye. The receiving pan 56, with the shape marking 58, forms second positioning formations in the meaning of the invention.

The basic carrier 22 has, on its head side (top) opposite the foot part 26, a supporting surface 60 for the auxiliary carrier 24. Suitable positioning formations 62, 64 on the basic carrier 22 ensure that the auxiliary carrier 24 can be placed on the supporting surface 60 only in a single (horizontal) position. The support state of the auxiliary carrier 24 on the object carrier 22 is shown in FIG. 5. The above-mentioned positioning formations 62, 64 form first positioning formations in the meaning of the invention. In the shown example, the positioning formation 64 is formed by a fin which rises from the supporting surface 60, and which when the auxiliary carrier 24 is placed dips into a complementarily formed groove 66 (see FIG. 3) which is formed on the underside of the auxiliary carrier 24. On the other hand, the positioning formation 62 is implemented as a lateral delimiting wall, which follows at least part of the edge contour of the auxiliary carrier 24 and ensures additional positioning stabilisation of the auxiliary carrier 24 on the basic carrier 22.

According to FIG. 6, a fan (ventilator) 68, which is controlled by control electronics which are arranged on a printed circuit board 70 which is also received in the basic carrier 22, is housed in the basic carrier 22. Via an electrical plug connection 72, electric current can be supplied to the printed circuit board 70 and thus the fan 68. The air current which the fan 68 generates escapes through a ventilation opening 74, which is positioned so that the air flow which escapes from the ventilation opening 74 flows away via the test lamina 28, which is lying in the receiving pan 56. In this way, ablation dust which can result from the laser processing of the test lamina 28 can be blown away from the test lamina 28. Alternatively, sucking this ablation dust away using an extractor fan is conceivable.

On the head side of the basic carrier 22, a spirit level 76 is also provided, and enables the user to align the basic carrier 22 on the examination table 10 by eye, so that horizontality of the supporting surface 60 and consequently of the auxiliary carrier 24 to be placed on it is set up. The regularly existing pliancy of the padding material of the head part 14 of the examination table 10 allows, within certain limits, alignment of the basic carrier 22, which is inserted into the head recess of the head part 14.

Although by using the spirit level 76 sufficiently precise horizontalisation of the supporting surface 60 for the purposes of the calibration procedure is achievable, because of the above-mentioned pliancy of the padding material of the head part 14 it is usually unavoidable that the position of the basic carrier 22 in the horizontal plane varies from case to case in a translatory or/and rotatory manner. The consequence of this is that the auxiliary carrier 24 and thus the test lamina 28 can from case to case be at a different position in the horizontal plane and also with a different orientation in the horizontal plane. If such case by case variations of position and orientation of the test lamina 28 on the basic carrier 22 are not compensated for by corresponding translatory and rotatory adjustment of the ablation pattern formed by the test ablations, the result is finally that on the measuring head 20 the measuring tips 32 can no longer dip precisely into the ablation craters. The result would be corresponding measurement errors.

Therefore, in the shown example, on the head side of the basic carrier 22, a pattern of a total of three optically detectable alignment marks 80, 82, 84 arranged at a distance from each other is formed, alignment mark 80 being central to the test lamina 28 if the latter is placed properly on the basic carrier 22 (by means of the auxiliary carrier 24). On the basis of the alignment mark 80, a position of the object carrier 22 in the horizontal plane can be determined. The two other alignment marks 82, 84 are, for example, on a common straight line with alignment mark 80. They make it possible to determine an orientation of the basic carrier 22 in the horizontal plane.

A camera 86, shown in FIG. 1, is used to take a picture of the head side of the basic carrier 22, suitable image analysis software in the control unit 18 recognising the alignment marks 80, 82, 84 from the picture data supplied by the camera 86, and determining information about the position and orientation of the pattern formed by the marks 80, 82, 84 in a coordinate system of the laser device 12. Depending on this determined position and orientation information, the control unit 18 then defines the shooting positions for the laser radiation pulses with which the test ablations are to be generated, in the coordinate system of the laser device 12. This mechanism makes the calibration procedure for the user specially simple, since he or she has to expend only relatively little effort on mounting the basic carrier 22 on the examination table 10, and only has to ensure a maximally horizontal alignment of the basic carrier 22 using the spirit level 76.

The basic carrier 22 is also implemented with a monitoring or/and warning light 88, which in the shown example is also arranged on the head side of the basic carrier 22, and can give optical indications for different purposes. For example, the lamp 88 can be connected to the operation of the fan 68, and signal whether or not it is functioning.

In FIG. 1, in association with the basic carrier 22 (in general: with the object carrier device), a reading device 90, by means of which an identifying code provided on the test lamina 28 can be read, is indicated. For example, such an identifying code is indicated at 92 in FIG. 2 in the form of a bar code. The bar code 92 can have been printed in advance by the manufacturer of the test lamina 28, and uniquely identifies the test lamina 28. If the test lamina 28 is usable on both sides, i.e. is suitable on both the top and the underside for doing test ablations, a bar code 92 can be provided on both sides of the test lamina 28, and then uniquely identifies the relevant lamina side.

Before the test ablations are generated on the test lamina 28, the control unit 18, on the basis of the read bar code 92, can establish whether the test lamina 28, or its relevant lamina side, has already been used. For this purpose, for example, it can access a database, not shown in more detail in the figures, in which information about every test lamina which has already been used is stored. If the control unit 18 establishes that the just read test lamina 28 is new, it releases the laser device 12 for emitting laser radiation. On the other hand, if the control unit 18 establishes that an already used test lamina, which the user for example only unintentionally wanted to use again, is involved, the control unit 18 can output a warning indication via a loudspeaker 94 or another suitable output device, and block the laser device 12 against emitting laser radiation.

Because it receives the measurement signals which are captured by the measuring probes 30 and supplied by the measuring head 20, the control unit 18 can store the measurement results together with the identifying code of the relevant test lamina electronically in an archive, if required also storing additional information such as the date or/and time of the test. Alternatively or additionally to such archiving in a separate archive, the test device can include a marking device which is provided, for example, on or in the measuring head 20, and by means of which the measurement results—if required together with date or/and time—are written in coded or uncoded form directly on the relevant test lamina 28. In this case, it can be enough to archive just the test lamina 28, with no accompanying electronic archiving.

In FIG. 1, a marking device 96, which is shown in association with the basic carrier 22 (in general: with the object carrier device), is also drawn schematically. This marking device 96 can, for example, be used to provide the test lamina 28, after the laser processing, with permanent marking, the presence of which indicates that the relevant lamina has already been used. The reading device 90 can then be set up, for example, alternatively or additionally to capturing a bar code or other code, to test the presence or absence of such a use marking on the test lamina 28.

The invention claimed is:

1. A method comprising:
  making, with pulsed laser radiation from a laser device, multiple test ablations on a test surface, the multiple test ablations formed in an arrangement corresponding to a relative spatial arrangement of a plurality of measuring probes on a measuring head of a separate test device;
  aligning a shape marking on the test surface with a complimentary shape marking on the test device to ensure a single relative angle of rotation orientation between the test surface and the measuring head, wherein the relative spatial arrangement of the multiple test ablations align with the plurality of measuring probes on the measuring head of the test device when the test surface and the measuring head are arranged in the single relative angle of rotation;
  simultaneously measuring, with the separate test device, a depth of each of the test ablations using the multiple measuring probes of the measuring head; and
  determining a relationship between a pulse energy of the pulsed laser radiations that formed each of the multiple test ablations and the depth of each of the test ablations.

2. The method of claim 1, wherein the measuring head includes three measuring probes.

3. The method of claim 1, wherein the test surface comprises a test disc with a circular outline, and wherein the measuring probes are arranged in the measuring head at equal angular intervals along an imaginary circular line.

4. The method of claim 3, wherein the test disc and the measuring head each include an index marking for aligning the test surface and the measuring head in the single relative angle of rotation.

5. The method of claim 4, wherein the index markings are implemented as color markings.

6. The method of claim 3, wherein the shape marking of the test disc comprises a cut off edge of a segment of the circular course of the test disc, and wherein the test device includes a receiving area with the complimentary shape marking.

7. The method of claim 1, further comprising:
  reading, with a reading device, an identifying code on a test object which forms the test surface.

* * * * *